(12) United States Patent
Shinoda et al.

(10) Patent No.: US 8,859,030 B2
(45) Date of Patent: Oct. 14, 2014

(54) METHOD FOR PRODUCING MEDICAL DEVICE

(71) Applicant: Terumo Kabushiki Kaisha, Shibuya-ku (JP)

(72) Inventors: Sayaka Shinoda, Fujinomiya (JP); Kazuya Omata, Fujinomiya (JP); Satoshi Sawada, Fujinomiya (JP); Takao Anzai, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

(21) Appl. No.: 13/693,791

(22) Filed: Dec. 4, 2012

(65) Prior Publication Data

US 2013/0095226 A1    Apr. 18, 2013

Related U.S. Application Data

(63) Continuation of application No. PCT/JP2011/062414, filed on May 30, 2011.

(30) Foreign Application Priority Data

Jun. 16, 2010  (JP) .................. 2010-137630
Aug. 23, 2010  (JP) .................. 2010-186574

(51) Int. Cl.

| | |
|---|---|
| *A61M 25/00* | (2006.01) |
| *B05D 3/10* | (2006.01) |
| *C09D 5/00* | (2006.01) |
| *A61L 29/08* | (2006.01) |
| *A61L 31/14* | (2006.01) |
| *A61L 31/10* | (2006.01) |
| *A61L 29/06* | (2006.01) |
| *A61L 29/14* | (2006.01) |
| *A61L 31/06* | (2006.01) |
| *C08G 69/40* | (2006.01) |
| *C08L 77/06* | (2006.01) |
| *C08L 77/02* | (2006.01) |

(52) U.S. Cl.
CPC ....... *C09D 5/00* (2013.01); *C08G 69/40* (2013.01); *A61L 29/085* (2013.01); *A61L 31/14* (2013.01); *C08L 77/06* (2013.01); *A61L 31/10* (2013.01); *A61L 2400/10* (2013.01); *A61L 29/06* (2013.01); *A61L 29/14* (2013.01); *C08L 77/02* (2013.01); *A61L 31/06* (2013.01)
USPC ............ 427/2.1; 428/2.28; 428/2.3; 428/299; 428/307; 428/322

(58) Field of Classification Search
USPC ........ 427/2.1, 2.24, 2.25, 2.28, 299, 307, 322
See application file for complete search history.

(56) References Cited

U.S. PATENT DOCUMENTS 3,240,620 A * 3/1966 Atwell .................. 442/150
3,721,598 A * 3/1973 Marcey .................. 156/307.3

(Continued)

FOREIGN PATENT DOCUMENTS

| CA | 1234656 A | * | 4/1988 |
| JP | 49061496 A | * | 6/1974 |

(Continued)

OTHER PUBLICATIONS

International Search Report (PCT/ISA/210) issued on Jun. 21, 2011, by the Japanese Patent Office as the International Searching Authority for International Application No. PCT/JP2011/062414.
Chinese Office Action issued on Dec. 4, 2013, in corresponding Chinese Patent Application No. 201180014969.9, and English translation thereof.

*Primary Examiner* — Cachet Sellman
(74) *Attorney, Agent, or Firm* — Buchanan Ingersoll & Rooney PC

(57) ABSTRACT

A method for firmly fixing a hydrophilic polymer on a polyamide surface involves applying a solution containing a phenolic compound to a base material of which at least a part of the surface is a polyamide, and coating the base material with a hydrophilic polymer after applying the solution.

18 Claims, 6 Drawing Sheets

(56) References Cited

U.S. PATENT DOCUMENTS

| | | | |
|---|---|---|---|
| 5,091,205 A * | 2/1992 | Fan | 427/2.28 |
| 5,670,558 A | 9/1997 | Onishi et al. | |
| 5,702,754 A | 12/1997 | Zhong | |
| 5,985,437 A * | 11/1999 | Chappell et al. | 428/336 |
| 6,048,620 A | 4/2000 | Zhong | |
| 6,540,698 B1 | 4/2003 | Ishii | |
| 7,588,659 B2 * | 9/2009 | Yoshino et al. | 156/330.9 |
| 2002/0120333 A1* | 8/2002 | Keogh et al. | 623/11.11 |
| 2006/0084788 A1* | 4/2006 | Yoshino et al. | 528/495 |
| 2007/0016169 A1* | 1/2007 | Utas et al. | 604/544 |
| 2008/0248210 A1* | 10/2008 | Kondos et al. | 427/412.1 |
| 2009/0155519 A1* | 6/2009 | Lee | 428/67 |

FOREIGN PATENT DOCUMENTS

| | | |
|---|---|---|
| JP | 8-033704 A | 2/1996 |
| JP | 8-257112 A | 10/1996 |
| JP | 8-317970 A | 12/1996 |
| JP | 11-319071 A | 11/1999 |
| JP | 2001-145695 A | 5/2001 |
| JP | 2007-289299 A | 11/2007 |
| JP | 2007-325639 A | 12/2007 |
| JP | 2008-119022 A | 5/2008 |

* cited by examiner

METHOD FOR PRODUCING MEDICAL DEVICE

CROSS REFERENCES TO RELATED APPLICATIONS

This application is a continuation of International Application No. PCT/JP2011/062414 filed on May 30, 2011 and claims priority to Japanese Patent Application No. 2010-137630 filed on Jun. 16, 2010 and Japanese Patent Application No. 2010-186574 filed on Aug. 23, 2010, the entire content of all three of which is incorporated herein by reference.

TECHNICAL FIELD

The present invention generally relates to a method for producing a medical device.

BACKGROUND DISCUSSION

Medical devices to be inserted into a living body, such as catheters and guide wires, should exhibit excellent lubricity to reduce damage to living body tissue such as blood vessel and to enhance operability for the operator. For this purpose, a method of coating a base material surface with a hydrophilic polymer having lubricity has been developed and put to practical use. In such medical devices, elution or peeling of the hydrophilic polymer from the base material surface imposes a problem, from the viewpoint of retention of safety and/or operability.

To avoid such a problem, U.S. Pat. No. 5,670,558 discloses a medical device in which a surface lubricating layer is formed on a base material surface by a method in which the base material surface is impregnated with a polymer solution containing a mixture of a hydrophilic polymer having a reactive functional group in its molecule and a polymer having a functional group capable of reacting with the reactive functional group, and thereafter the polymers are allowed to react with each other to form a cross-linked structure, thereby forming an insoluble polymer. According to the method described in U.S. Pat. No. 5,670,558, the surface lubricating layer can be fixed on the base material firmly to a certain extent. Especially, in the case where the base material itself is swelled with the hydrophilic polymer solution, the base material and the hydrophilic polymer constituting the surface lubricating layer form an interpenetrating network structure, whereby firm fixation can be achieved.

According to the technology described in U.S. Pat. No. 5,670,558, however, there is the following problem. When the base material is not easily swelled with the hydrophilic polymer solution, the hydrophilic polymer constituting the surface lubricating layer is fixed on the base material by only the insolubilization owing to cross-linking or the like. Therefore, the possibility of peeling of the surface lubricating layer in this case is higher as compared with the case of a base material capable of forming the interpenetrating network structure by being swelled with the hydrophilic polymer solution. Polyamide resin is a representative resin for wide use as base material for medical devices such as catheters, guide wires and indwelling needles. Polyamide resin is a crystalline polymer in which a hydrogen bond can be formed between amide linkages of different polymer chains, and strong intermolecular forces are acting in the crystalline region. Therefore, the polyamide resin is not easily swelled with a hydrophilic polymer solution, and it is difficult to form an interpenetrating network structure. Accordingly, the surface lubricating layer is formed only by the insolubilization of the hydrophilic polymer. Thus, the problem of easy peeling of the surface lubricating layer has existed. There is thus a need for a method by which a hydrophilic polymer can be more firmly fixed on a polyamide surface that is not easily swellable with a hydrophilic polymer solution.

SUMMARY

Following investigative and developmental work, the inventors here discovered that by applying a solution containing a phenolic compound to a base material of which at least a part of the surface is a polyamide and thereafter coating the base material with a hydrophilic polymer, it is possible to obtain a medical device in which a hydrophilic polymer is firmly fixed.

According to an aspect of the disclosure here, a method for producing a medical device includes applying a solution containing a phenolic compound to a base material of which at least a part of a surface is a polyamide; and coating the base material with a hydrophilic polymer after the application of the solution containing the phenolic compound. The method disclosed here allows a hydrophilic polymer to be relatively firmly fixed on a polyamide surface.

According to another aspect, a method for producing a medical device comprises: applying a solution containing a phenolic compound to a medical device, wherein the medical device is sized and configured to be positioned in a living body, and is made of a base material and possesses a surface, with at least a part of the surface being composed of a polyamide. The application of the solution to the medical device comprises applying the solution containing the phenolic compound to the medical device so that the solution containing the phenolic compound contacts the part of the surface of the base material that is composed of the polyamide. The method also involves coating the base material with a hydrophilic polymer after applying the solution containing the phenolic compound, with the hydrophilic polymer being coated onto the part of the surface of the base material to which is applied the solution containing the phenolic compound.

DETAILED DESCRIPTION

Figure 1:
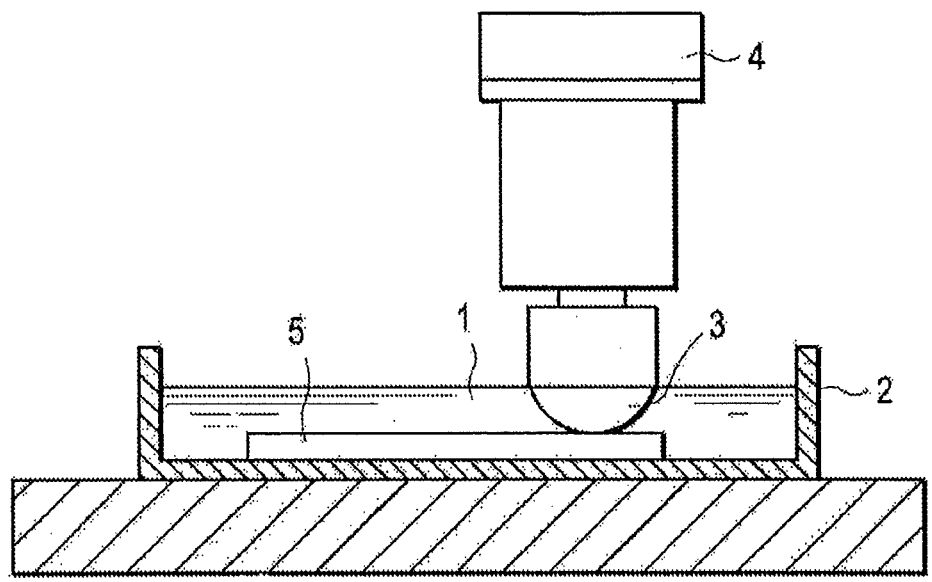
FIG. 1 is a schematic illustration of a friction measuring apparatus for use in evaluation of surface lubricity retention, in which numeral 1 denotes water, 2 a petri dish, 3 a SUS-made spherical probe, 4 a weight, and 5 a sample.
Figure 2:
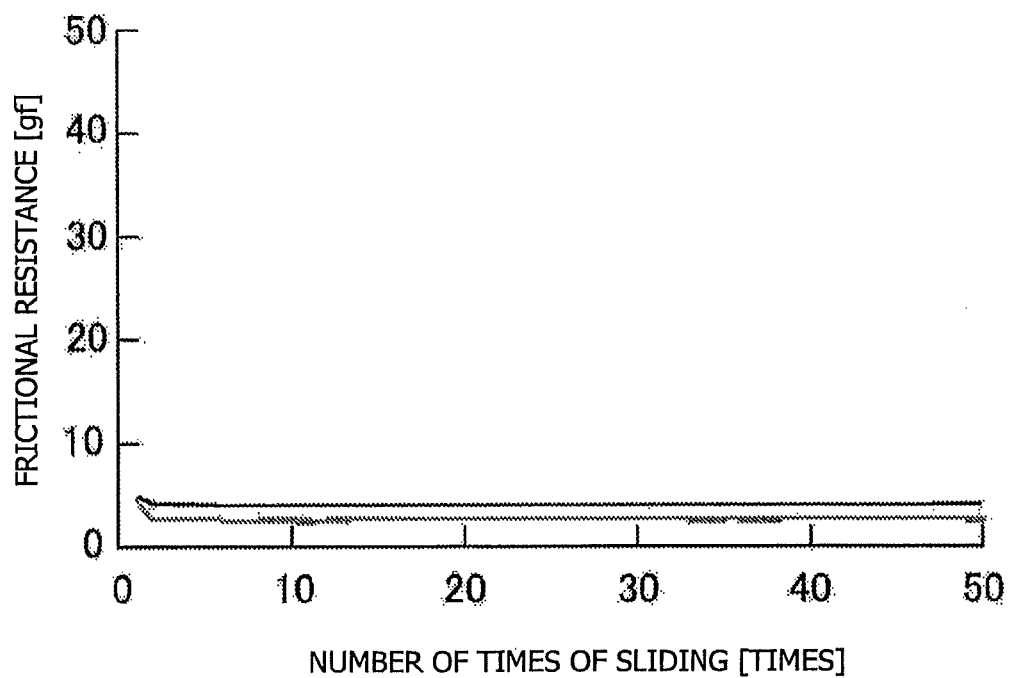
FIG. 2 shows the evaluation results of surface lubricity retention for a sheet (sample) obtained in Example 1.
Figure 3:
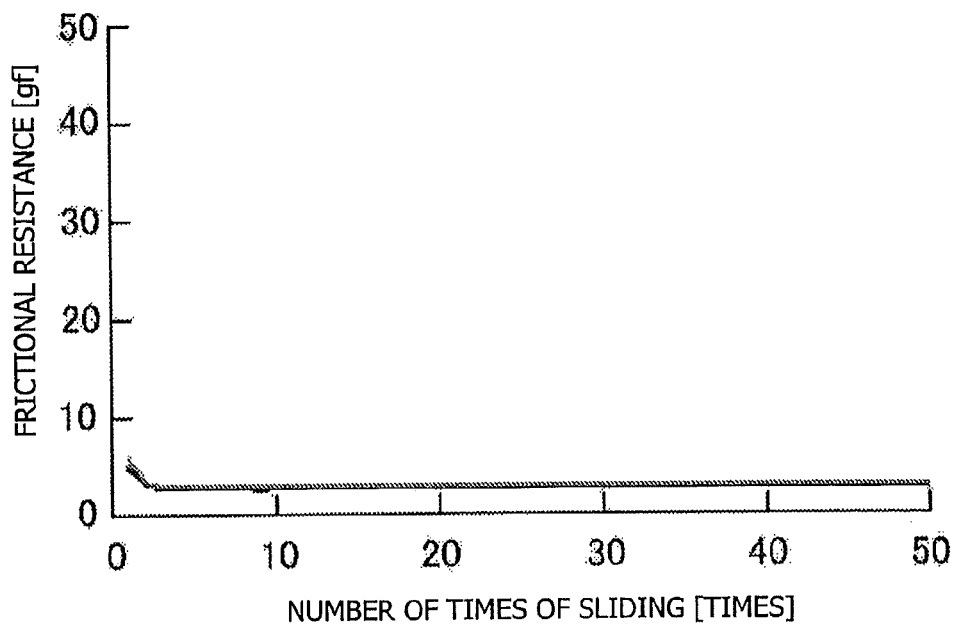
FIG. 3 shows the evaluation result of surface lubricity retention for a sheet (sample) obtained in Example 2.
Figure 4:
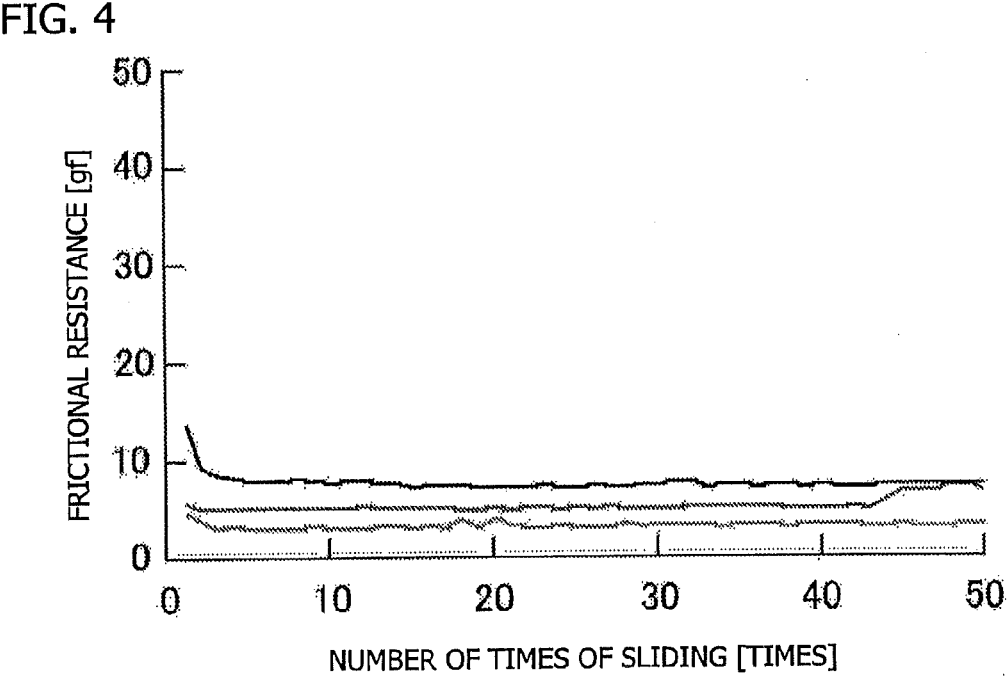
FIG. 4 shows the evaluation result of surface lubricity retention for a sheet (sample) obtained in Example 3.
Figure 5:
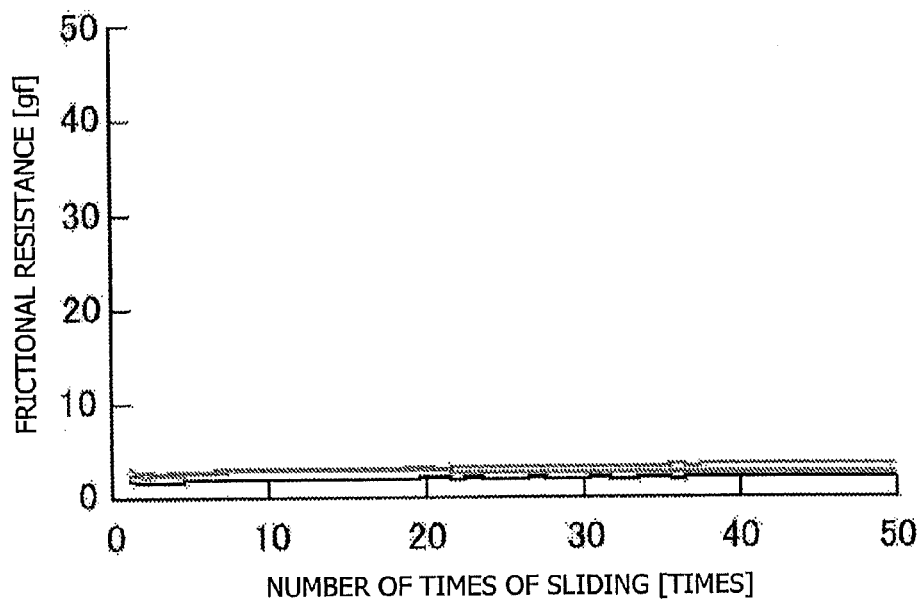
FIG. 5 shows the evaluation result of surface lubricity retention for a film (sample) obtained in Example 4.

The disclosure here involves a method for producing a medical device that includes applying a solution containing a phenolic compound to a base material of which at least a part of a surface is a polyamide, and coating the base material with a hydrophilic polymer after the application of the solution containing the phenolic compound.

The polyamide is a crystalline polymer in which a hydrogen bond is formed between amide linkages of different polymer chains. It is known that in a crystalline region, strong intermolecular forces act, solubility in organic solvent is low, and only an extremely slight change in response to acetone or the like is observed. When a solution containing a phenolic compound is applied to a base material of which at least a part of the surface is a polyamide, however, the polyamide is partly made amorphous by the action of the phenolic compound contained in the solution, whereby the spacing between polymer chains is broadened. In addition, the hydrophilic polymer coating the base material enter the broadened spacing between the polymer chains of the polyamide, enabling the formation of an interpenetrating network structure in which the polyamide and the hydrophilic polymer are entangled with each other in an amorphous form. Accordingly, the hydrophilic polymer (surface lubricating layer) can be firmly fixed on the surface of the polyamide which is difficult to swell.

A method for producing a medical device according to one example disclosed here will now be described. It is to be noted, however, that the present invention is not limited to the details of the method discussed below.

Applying a Solution Containing a Phenolic Compound to a Base Material

In this aspect of the method, a solution containing a phenolic compound is applied to a base material of which at least a part of the surface is a polyamide.

Base Material

The expression that the base material is a material of which "at least a part of the surface is a polyamide" means that at least a part of the surface of the base material is composed of a polyamide, and the base material is not limited in any way to a material of which the whole part (entire part) is composed (formed) of a polyamide. Thus, those materials wherein a surface of a base material formed of a hard reinforcing material such as metallic materials and ceramic materials is coated with a polyamide more flexible than the reinforcing material such as metallic materials by an appropriate method (any of conventionally known methods such as dipping, spraying, and application or printing) and those materials wherein at least a part of the surface is a polyamide as a result of composite formation (appropriate reaction treatment) between the polyamide and the metallic material or the like used as a base material, are included as the base material described herein. Further, the base material may be a multilayer structure obtained by laminating different materials in multiple layers, or a structure (composite body) obtained by interlinking members formed of different materials for different parts of the medical device.

In addition, the proportion or part of the surface area composed (formed) of the polyamide or coated with the polyamide, based on the whole surface of the base material, is not limited to a specific value, insofar as at least a part of the surface of the base material is composed of the polyamide and the hydrophilic polymer (surface lubricating layer) can be subsequently firmly fixed on the base material surface.

The polyamide which can be used for the base material is not specifically limited, but may be appropriately selected so that it can sufficiently exhibit a function as an optimum base material, according to the use such as catheter, guide wire or indwelling needle. Examples of the material is not particularly limited insofar as it is a polymer having an amide linkage. Examples of the material include homopolymers such as polytetramethylene adipamide (nylon 46), polycaprolactam (nylon 6), polyhexamethylene adipamide (nylon 66), polyhexamthylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylene diammonium adipate copolymer (nylon 6/66), etc., and aromatic polyamides such as adipic acid-metaxylenediamine copolymer, copolymers of hexamethylene diamine with m- or p-phthalic acid, etc.

Furthermore, polyamide elastomers which are block copolymers having nylon 6, nylon 66, nylon 11, nylon 12 or the like as a hard segment and having a polyalkylene glycol, polyether, aliphatic polyester or the like as a soft segment can also be used as the base material of the medical device according to the present invention. The above-mentioned polyamides may be used either singly or in combination of two or more of them.

In addition, as the polyamides, synthesized ones may be used and commercialized ones may be used. Examples of the commercialized polyamides include polyamides such as Grilamid L25 (produced by EMS-CHEMIE (Japan) Ltd.), etc., and polyamide elastomers such as Grilamid ELG6260, Grilamid ELG5660 (both produced by EMS-CHEMIE (Japan) Ltd.), etc.

Examples of materials other than the polyamides that can be used for the base material include: various inorganic materials such as various metallic materials, for example, various stainless steels (SUS) such as SUS304, SUS316L, SUS420J2, SUS630, etc., gold, platinum, silver, copper, nickel, cobalt, titanium, iron, aluminum, tin, nickel-titanium alloys, cobalt-chromium alloys, zinc-tungsten alloys and their alloys, etc., and various ceramic materials; metal-ceramic composite materials; and polymeric materials such as polyolefin resins, e.g., polyethylene resin such as straight-chain low-density polyethylene, low-density polyethylene, high-density polyethylene, etc., and polypropylene resin, etc., epoxy resins, urethane resins, diallyl phthalate resins (allyl resins), polycarbonate resins, fluoro-resins, amino resins (urea resins, melamine resins, benzoguanamine resins), polyester resins, styrol resins, acrylic resins, polyacetal resins, vinyl acetate resins, phenol resins, vinyl chloride resins, silicone resins (silicon resins), etc. These materials may be used either singly or in combination of two or more of them. From these materials, an optimum material for the base material may be appropriately selected according to the use such as a catheter, a guide wire or an indwelling needle.

Phenolic Compound

The phenolic compound for use in the method disclosed here is not limited insofar as it can make the polyamide amorphous. Specific examples of the phenolic compound include 1,2-dihydroxybenzene (catechol), 1,3-dihydroxybenzene (resorcinol), 1,4-dihydroxybenzene (hydroquinone), 1,2,4-trihydroxybenzene, 1,6-dihydroxynaphthalene, 2,2'-biphenol, 4,4'-biphenol, and t-butylhydroxyanisole. These phenolic compounds may be used either singly or in combination of two or more of them. Among these phenolic compounds, preferred are 1,3-dihydroxybenzene (resorcinol) and t-butylhydroxyanisole, in view of their conspicuous ability to make the polyamide amorphous.

In this application portion of the method, the solution containing the above-mentioned phenolic compound is applied to the base material. The solvent used for the solution is not particularly limited. Examples of the solvent include alcohols such as methanol, ethanol, n-propyl alcohol, isopropyl alcohol, n-butyl alcohol, t-butyl alcohol, etc., N,N'-dimethylformamide, N,N'-dimethylacetamide, ethylene chloride, chloroform, acetone, tetrahydrofuran, and dioxane. These solvents may be used either singly or in combination of two or more of them. Among these solvents, more preferred are methanol and tetrahydrofuran, in view of their solubility. The concentration of the above-mentioned phenolic compound in the solution is also not particularly limited. From the viewpoint of making the polyamide amorphous more efficiently, however, the concentration is preferably 10 to 75 wt %, more preferably 20 to 50 wt %. It is to be noted that even a concentration outside the above-mentioned range can be sufficiently utilized, insofar as it is within such a range as not to influence the effect of the present invention.

The method for applying the solution containing the phenolic compound to the base material is not specifically limited. The method used can be conventionally known methods, examples of which include a dipping method, an applying or printing method, a spraying method, a spin coating method, and a mixed solution impregnated sponge coating method. Among these method, preferred is the dipping method.

In the case where the dipping method is used, the dipping conditions for the solution containing the phenolic compound used for the dipping are not limited to certain conditions. For example, the dipping time is not specifically restricted, and is preferably five seconds to thirty minutes, more preferably five seconds to five minutes. When the dipping time is within such a range, the polyamide is sufficiently made amorphous, the spacing between the polymer chains of the polyamide can be broadened, and the hydrophilic polymer is permitted to enter into the broadened spacing between the polymer chains of the polyamide, resulting in amorphous entanglement.

Coating with a Hydrophilic Polymer

This aspect of the method involves coating the base material with a hydrophilic polymer after the solution containing the phenolic compound is applied to the base material. The hydrophilic polymer used for coating forms a surface lubricating layer on the outer surface of the base material.

Here, the surface lubricating layer may be formed so that it covers the entire surface of the base material, or may alternatively be formed only on a surface portion where the surface is required to have lubricity when wetted.

Hydrophilic Polymer

The hydrophilic polymer can be obtained, for example, by (co)polymerization of a hydrophilic monomer or monomers. Here, the hydrophilic polymer is not specifically limited insofar as it has in its structure a constitutional unit derived from a hydrophilic monomer or monomers. Preferably, however, the hydrophilic polymer is a polymer formed from only a hydrophilic monomer or monomers, or a copolymer of a hydrophilic monomer and a monomer having a reactive functional group capable of a cross-linking reaction. In addition, the hydrophilic polymer preferably has a reactive functional group capable of a cross-linking reaction. Such a hydrophilic polymer as just-mentioned is not specifically restricted insofar as it has a reactive functional group capable of a cross-linking reaction. Preferably, however, the hydrophilic polymer is a block copolymer having both a block formed from a hydrophilic monomer and a block formed from a monomer having a reactive functional group.

Hydrophilic Monomer

The hydrophilic monomer may be any one that exhibits lubricity in a body fluid or an aqueous solvent. Examples of the hydrophilic monomer include acrylamides and derivatives thereof, vinylpyrrolidone, acrylic acid and methacrylic acid and derivatives thereof, and monomers having sugar or phospholipids in a side chain thereof. Preferable examples of the hydrophilic monomer include N-methylacrylamide, N,N'-dimethylacrylamide (DMAA), acrylamide, acryloylmorpholine, N,N'-dimethylaminoethyl acrylate, vinylpyrrolidone, 2-methacryloyloxyethylphosphorylcholine, 2-methacryloyloxyethyl-D-glycoside, 2-methacryloyloxyethyl-D-mannoside, vinyl methyl ether, and hydroxyethyl methacrylate. From the viewpoints of ease of synthesis and operability, preferred are N,N'-dimethylacrylamide and vinylpyrrolidone, and more preferred is N,N'-dimethylacrylamide. These hydrophilic monomers may be used either singly or in combination of two or more of them. As for the form of the polymer in the case of using two or more of these hydrophilic monomers, the polymer may be a block copolymer or a random copolymer.

The method for preparation (method for polymerization) of the hydrophilic polymer is not particularly limited. For example, the hydrophilic polymer can be prepared by using a conventionally known polymerization method, such as living radical polymerization method, polymerization method in which macromonomer is used, polymerization method in which a polymer initiator such as macro-azo initiator is used, and polycondensation method.

Monomer Having a Reactive Functional Group Capable of a Cross-Linking Reaction

The above-mentioned hydrophilic polymer may be a copolymer of the above-mentioned hydrophilic monomer and a monomer having a reactive functional group capable of a cross-linking reaction.

The monomer having a reactive functional group capable of a cross-linking reaction is not limited to a specific monomer. Examples of such a monomer include monomers having an epoxy group, such as glycidyl acrylate, glycidyl methacrylate, etc. and monomers having an isocyanate group, such as acryloyloxyethyl isocyanate. Among these monomers, preferred are the monomers having an epoxy group, such as glycidyl acrylate and glycidyl methacrylate, which are characterized in that the cross-linking reaction is accelerated by heat, which are insolubilized through formation of a cross-linked structure to thereby promise easy formation of a surface lubricating layer, and which are comparatively easy to handle. The hydrophilic polymers prepared by use of a monomer having an epoxy group is characterized in that the reaction rate in reaction by a heating operation or the like is more moderate (appropriate rate), as compared with the hydrophilic polymers prepared by use of a monomer having an isocyanate group. Therefore, the hydrophilic polymer prepared by use of a monomer having an epoxy group is easy to handle, since the reaction rate thereof is so moderate (appropriate rate) that it is possible at the time of reaction by a heating operation or the like, in other words, at the time of a cross-linking reaction between the reactive functional groups, to restrain or control gelation or solidification through the immediate reaction, which might lead to an enhanced density of crosslinks in the surface lubricating layer and to a lowered lubricity. These monomers having a reactive functional group capable of a cross-linking reaction may be used either singly or in combination of two or more of them.

In order to exhibit good lubricity, the hydrophilic polymer is preferably a hydrophilic polymer which is prepared by copolymerization of the hydrophilic monomer with the monomer having a reactive functional group capable of a cross-linking reaction and which has a reactive functional group capable of a cross-linking reaction. More preferably, the hydrophilic polymer is a block copolymer which has a block formed from the hydrophilic monomer and a block formed from the monomer having a reactive functional group capable of a cross-linking reaction. When the hydrophilic polymer is such a block copolymer as just-mentioned, good results can be obtained in regard of strength and lubricity of the surface lubricating layer.

The method for preparation (method for polymerization) of the hydrophilic polymer in which the hydrophilic monomer and the monomer having a reactive functional group capable of a cross-linking reaction are copolymerized with each other is also not specifically restricted, like the above-mentioned preparation (polymerization) method. The hydrophilic polymer here can be prepared, for example, by applying a conventionally known polymerization method, such as living radical polymerization method, polymerization method in which a macromonomer is used, polymerization method in which a polymer initiator such as macro-azo initiator is used, and polycondensation method.

In the case of forming a surface lubricating layer composed of the hydrophilic polymer, the base material to which a solution containing the phenolic compound has preliminarily been applied is dipped in a solution prepared by dissolving the hydrophilic polymer (hereinafter, this solution will be referred to also as "hydrophilic polymer solution"), followed by drying, and optionally followed by a heating treatment or the like. As a result, the hydrophilic polymer enters into the spacing between the polymer chains of polyamide, to form a surface lubricating layer, and, simultaneously, the surface lubricating layer can be firmly fixed on the base material. In the condition where the base material to which the phenolic compound has been applied is dipped in the hydrophilic polymer solution, the pressure in the system may be lowered to cause degassing and to cause the solution to rapidly penetrate minute and narrow internal surfaces of a medical device such as catheter, guide wire, indwelling needle, etc., thereby accelerating the formation of the surface lubricating layer.

The base material can be coated with the hydrophilic polymer by application of a conventionally known method such as applying/printing method, spraying method, spin coating method, mixed solution impregnated sponge coating method, etc., in place of the method in which the base material with the phenolic compound-containing solution preliminarily applied thereto is dipped in the hydrophilic polymer solution (dipping method).

In the following, detailed description will be made by taking as an example a mode in which the base material with the phenolic compound-containing solution preliminarily applied thereto is dipped in the hydrophilic polymer solution, to coat the base material surface with the hydrophilic polymer solution (coating solution), followed by a heating operation to put the hydrophilic polymer into a cross-linking reaction, thereby forming the surface lubricating layer. It is to be noted here, however, that the present invention is not limited in any way to the coating and reaction treating operations.

Examples of the solvent to be used to dissolve the hydrophilic polymer include N,N'-dimethylformamide (DMF), chloroform, acetone, tetrahydrofuran, dioxane, benzene, and methanol, but the solvent is not restricted to these solvents in any way. These solvents may be used either singly or in combination of two or more of them.

The concentration of the hydrophilic polymer solution for use in forming the surface lubricating layer is not particularly limited. From the viewpoint of realizing a uniform coating in a desired thickness, the concentration of the hydrophilic polymer in the hydrophilic polymer solution is 0.1 to 20 wt %, preferably 0.5 to 15 wt %, and more preferably 1 to 10 wt %. When the concentration of the hydrophilic polymer solution is less than 0.1 wt %, productivity may be lowered; for example, it may be necessary to repeat the above-mentioned dipping operation a plurality of times, in order to obtain the surface lubricating layer in a desired thickness. When the concentration of the hydrophilic polymer solution is in excess of 20 wt %, on the other hand, the viscosity of the hydrophilic polymer solution may be too high to realize coating with a uniform film; in this case, it may be difficult to quickly coat the minute and narrow internal surfaces of the medical device such as catheter, guide wire, indwelling needle, etc. However, even a concentration outside the above-mentioned range can be sufficiently utilized insofar as the concentration is within such a range as not to significantly influence the effect produced by the present invention.

In addition, in the case of using the dipping method, the dipping conditions in which the base material with the phenolic compound-containing solution preliminarily applied thereto is dipped in the hydrophilic polymer solution are not specifically limited. For example, the dipping time is not particularly limited, and is preferably five seconds to thirty minutes, more preferably five seconds to five minutes.

In the case where the hydrophilic polymer is a hydrophilic polymer having a reactive functional group capable of a cross-linking reaction, the hydrophilic polymer may be cross-linked by a heating treatment or the like to thereby form the surface lubricating layer.

It is sufficient that the conditions for such a heating treatment (reaction conditions) as just-mentioned are such as to enable proceeding (acceleration) of the cross-linking reaction of the hydrophilic polymer. Thus, the conditions (reaction conditions) can be appropriately determined according to the temperature characteristics (thermal resistance) of the polyamide of the base material.

For instance, the heating treatment temperature (a set temperature for a heating device such as a heating furnace) is preferably 40 to 150° C., more preferably 50 to 140° C. With the heating treatment temperature within such a range, the desired cross-linking reaction is accelerated sufficiently, and a desired effect can be obtained in a relatively short time.

The heating treatment time is not specifically restricted, insofar as it is in such a range that the cross-linking reaction of the hydrophilic polymer can proceed. The heating treatment time is preferably fifty minutes to fifty hours, more preferably thirty minutes to ten hours. With the heating treatment time within such a range, the cross-linking reaction proceeds efficiently, so that the amount of the uncross-linked hydrophilic polymer can be reduced, and the surface lubricity can be maintained for a relatively long time. In addition, it is advantageous on a manufacturing cost basis.

A pressure condition during the heating treatment, also, is not particularly limited. The heating treatment may be conducted at normal pressure (atmospheric pressure), or may be performed under a positively applied pressure or a reduced pressure. In the case where the reactive functional group capable of a cross-linking reaction that is possessed by the hydrophilic polymer is an epoxy group, a reaction catalyst such as a tertiary amine compound such as a trialkylamine compound and pyridine may be added to the hydrophilic polymer solution at an appropriate time and in an appropriate amount so that the cross-linking reaction can be accelerated. As a means (device) for heating, there can be utilized, for example, an oven, a drier, and a microwave heater.

Examples of methods other than the heating treatment by which to cause the cross-linking reaction of the hydrophilic polymer to proceed include irradiation with light, electron beams, radiation or the like. The methods other than the heating treatment are not limited to these examples.

The thickness of the surface lubricating layer can be such that the excellent surface lubricity during use can be exhibited permanently. Specifically, it is preferable that the thickness of the surface lubricating layer when unswollen is 0.5 to 5 μm, preferably 1 to 5 μm, and more preferably 1 to 3 μm. Where the thickness of the surface lubricating layer when unswollen is less than 0.5 μm, it is difficult to form a uniform coating film, and it may be impossible for the layer to sufficiently exhibit surface lubricity when wetted. Where the thickness of the surface lubricating layer when unswollen is more than 5 μm, on the other hand, swelling of the thick surface lubricating layer may produce the following problem. In the case of inserting the medical device into a blood vessel or the like in a living body, specifically at the time of passing the medical device through a part (for example, the inside of a peripheral blood vessel) where the clearance between the blood vessel or the like and the medical device is small, the internal tissue of the blood vessel or the like may be damaged, or it may be difficult to pass the medical device through the part.

After the surface lubricating layer is formed, it is possible to wash away the excess of the hydrophilic polymer with an appropriate solvent so that only the hydrophilic polymer firmly fixed on the base material is left in situ.

The surface lubricating layer formed in this manner exhibits lubricity by absorbing water at a patient's body temperature (30 to 40° C.).

Use of Medical Device

Examples of the use for the medical device obtained by the producing method disclosed here includes those which have surface lubricity in aqueous liquid such as body fluid and physiological saline and which enables enhancement of operability or reduction of damages to tissues or mucous membrane. The medical device can thus be configured and sized to be positioned in a living body inclusive of blood vessels. Specific examples include not only catheters, guide wires, indwelling needles and the like for use in blood vessels, but also the following medical devices.

Catheters to be orally or transnasally inserted or set indwelling in the digestive organ, such as stomach tube catheter, hyperalimentation catheter, feeding tube, etc.

Catheters to be orally or transnasally inserted or set indwelling in the respiratory tract or trachea, such as oxygen catheter, oxygen cannula, tube or cuff of endotracheal tube, tube or cuff of tracheostomy tube, endotracheal suction tube, etc.

Catheters to be inserted or set indwelling in the urethra or ureter, such as urethral catheter, urinary catheter, catheter or balloon of balloon catheter, etc.

Catheters to be inserted or set indwelling in various body lumens, organs or tissues, such as suction catheter, drainage catheter, rectal catheter, etc.

Catheters to be inserted or set indwelling in blood vessels, such as indwelling needle, IVH catheter, thermodilution catheter, angiography catheter, vasodilation catheter, dilator, introducer and the like, or guide wires, stylets and the like for these catheters.

Stents as well as artificial blood vessel, artificial trachea, artificial bronchial tube, etc.

Medical devices for extracorporeal circulation therapy (artificial lung, artificial heart, artificial kidney, etc.) and circuits for them.

EXAMPLES

Effects associated with the method disclosed here are described more in detail below by use of the following Examples and Comparative Examples. It is to be noted, however, that the technical scope of the present invention is not limited to only the following Examples.

Example 1

A pressed sheet of a polyamide elastomer (Grilamid ELG5660, produced by EMS-CHEMIE (Japan) Ltd.) was dipped in a 25 wt % methanol solution of 1,3-dihydroxybenzene for one minute. Next, the sheet was dipped in a 1.5 wt % tetrahydrofuran (THF) solution of a block copolymer [p(DMAA-b-GMA)] (DMAA:GMA=12:1 (by mol)) which has poly(N,N'-dimethylacrylamide) (DMAA) as a block formed from a hydrophilic monomer and polyglycidyl methacrylate (GMA) as a block formed from a monomer having a reactive functional group capable of a cross-linking reaction. Thereafter, the sheet was dried (subjected to a heating treatment) in an oven at 50° C. for two hours, to obtain a sheet coated on its surface with a surface lubricating layer formed of p(DMAA-b-GMA).

Example 2

A sheet coated on its surface with a surface lubricating layer formed of p(DMAA-b-GMA) was obtained in the same manner as in Example 1, except that the 25 wt % methanol solution of 1,3-dihydroxybenzene in Example 1 was replaced by a 50 wt % methanol solution of t-butylhydroxyanisole.

Example 3

A sheet coated on its surface with a surface lubricating layer formed of p(DMAA-b-GMA) was obtained in the same manner as in Example 1, except that the pressed sheet of the polyamide elastomer (Grilamid ELG5660, produced by EMS-CHEMIE (Japan) Ltd.) in Example 1 was replaced by a pressed sheet of a polyamide (Grilamid L25, produced by EMS-CHEMIE (Japan) Ltd.).

Example 4

A biaxially oriented film of a polyamide elastomer (Grilamid ELG5660, produced by EMS-CHEMIE (Japan) Ltd.) was dipped in a 25 wt % methanol solution of 1,3-dihydroxybenzene for three minutes. Next, the biaxially oriented film was dipped in a 3.5 wt % THF solution of a block copolymer [p(DMAA-b-GMA)] (DMAA:GMA=12:1 (by mol)) which has poly(N,N'-dimethylacrylamide) (DMAA) as a block formed from a hydrophilic monomer and polyglycidyl methacrylate (GMA) as a block formed from a monomer having a reactive functional group capable of a cross-linking reaction. Thereafter, the biaxially oriented film was dried at room temperature (25° C.) for 180 minutes, to obtain a film coated on its surface with a surface lubricating layer formed of p(DMAA-b-GMA).

Comparative Example 1

A sheet coated on its surface with a surface lubricating layer formed of p(DMAA-b-GMA) was obtained in the same manner as in Example 1, except that the dipping in the 25 wt % methanol solution of 1,3-dihydroxybenzene in Example 1 was not conducted.

Comparative Example 2

A sheet coated on its surface with a surface lubricating layer formed of p(DMAA-b-GMA) was obtained in the same manner as in Example 3, except that the dipping in the 25 wt % methanol solution of 1,3-dihydroxybenzene in Example 3 was not conducted.

Comparative Example 3

A film coated on its surface with a surface lubricating layer formed of p(DMAA-b-GMA) was obtained in the same manner as in Example 4, except that the dipping in the 25 wt % methanol solution of 1,3-dihydroxybenzene in Example 4 was not conducted.

Evaluation of Surface Lubricity Retention

The sheets produced in Examples 1 to 3 and Comparative Examples 1 and 2 and the films produced in Example 4 and Comparative Example 3 (hereafter "sheet" and "film" will be referred to also as "sample") were subjected to evaluation of surface lubricity retention by use of a friction measuring apparatus (Handy Tribomaster TL201, produced by Trinity Lab Inc.) and by the following method.

As shown in FIG. 1, a double coated tape was adhered to a glass-made petri dish 2, and each sample 5 was fixed on the adhesive surface of the double coated tape. The petri dish 2 was filled up with water 1, and the assembly was put on the friction measuring apparatus. Then, using a weight 4, a load of 300 g was exerted on a SUS-made spherical probe 3, and frictional resistance was measured while sliding the probe 3 over a distance of 20 mm at a velocity of 1,000 mm/min, repeatedly 50 times. In this case, the measurement was conducted three times (n=3) for each sample, and the measurement results were plotted in graphs, respectively.

Figure 6:
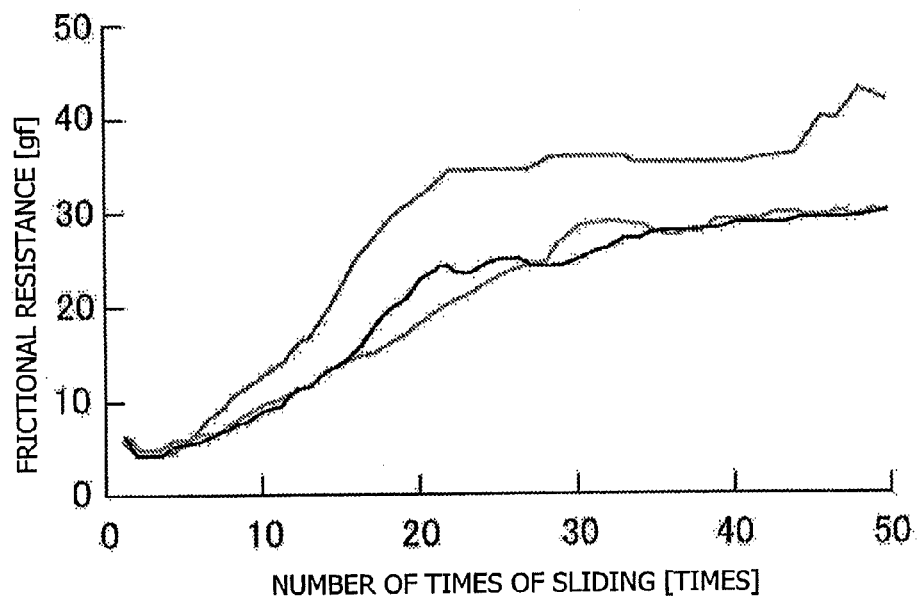
FIG. 6 shows the evaluation result of surface lubricity retention for a sheet (sample) obtained in Comparative Example 1.
Figure 7:
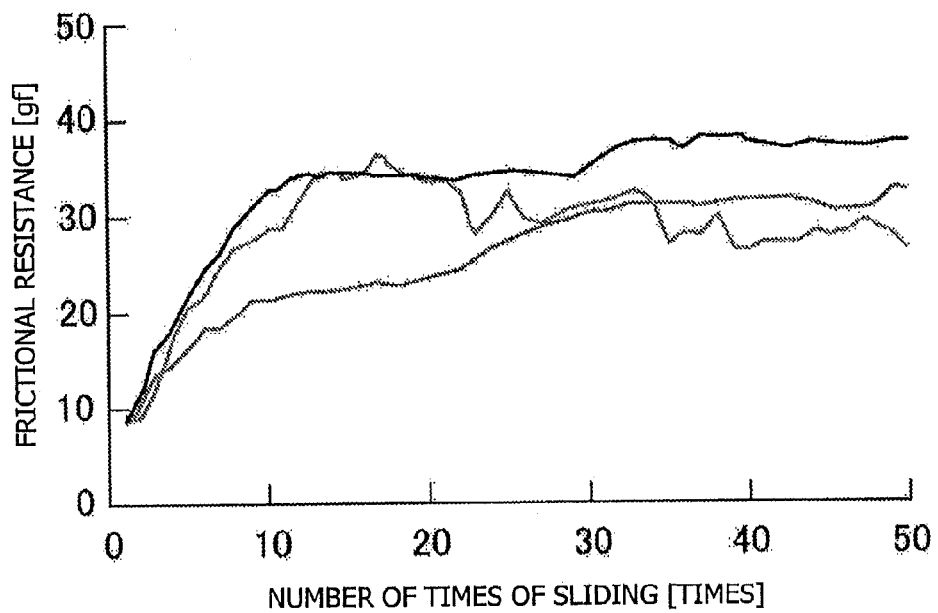
FIG. 7 shows the evaluation result of surface lubricity retention for a sheet (sample) obtained in Comparative Example 2.
Figure 8:
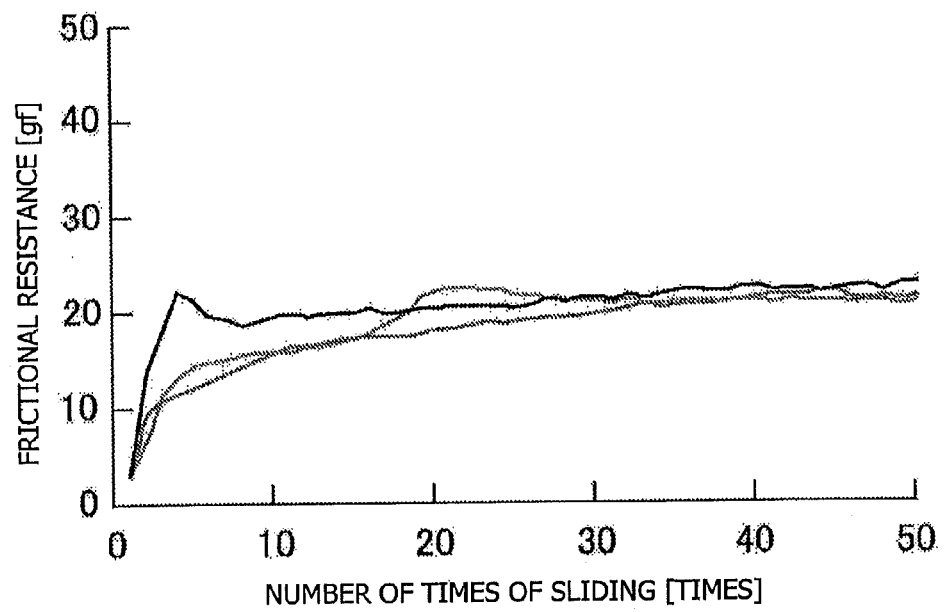
FIG. 8 shows the evaluation result of surface lubricity retention for a film (sample) obtained in Comparative Example 3.

The measurement results of surface lubricity retention for the samples produced in Examples 1 to 4 are shown in FIGS. 2 to 5 respectively, whereas the measurement results of surface lubricity retention for the samples produced in Comparative Examples 1 to 3 are shown in FIGS. 6 to 8, respectively. In Examples 1 to 4, every one of the samples showed a substantially constant low value of frictional resistance in a maintained manner, and showed stable surface lubricity retention during when the sliding was repeated 50 times. On the other hand, in Comparative Examples 1 to 3, though the samples showed lower values of frictional resistance in the beginning period, the frictional resistance increased due to peeling of the surface lubricating layer as the sliding was repeated; thus, the samples exhibited poor surface lubricity retention.

Example 5

A pressed sheet of a polyamide elastomer (Grilamid ELG5660, produced by EMS-CHEMIE (Japan) Ltd.) was dipped in a 5 wt % methanol solution of 1,3-dihydroxybenzene for one minute. Next, the sheet was dipped in a 10 wt % THF solution of poly(N,N'-dimethylacrylamide) (PDMAA, produced by Scientific Polymer Products, Inc.; molecular weight: 100,000) used as a hydrophilic polymer. Thereafter, the sheet was dried (heat-treated) in an oven at 50° C. for four hours, to obtain a sheet coated on its surface with a surface lubricating layer formed of PDMAA.

Comparative Example 4

A sheet coated on its surface with a surface lubricating layer formed of PDMAA was obtained in the same manner as in Example 5, except that the dipping in the 25 wt % methanol solution of 1,3-dihydroxybenzene was not conducted.

Example 6

A pressed sheet of a polyamide elastomer (Grilamid ELG5660, produced by EMS-CHEMIE (Japan) Ltd.) was dipped in a 25 wt % methanol solution of 1,3-dihydroxybenzene for one minute. Next, the sheet was dipped in a 10 wt % methanol solution of polyvinylpyrrolidone (PVP, produced by Wako Pure Chemical Industries, Ltd.; molecular weight: 360,000) used as a hydrophilic polymer. Thereafter, the sheet was dried (heat treated) in an oven at 50° C. for four hours, to obtain a sheet coated on its surface with a surface lubricating layer formed of PVP.

Comparative Example 5

A sheet coated on its surface with a surface lubricating layer formed of PVP was obtained in the same manner as in Example 6, except that the dipping in the 25 wt % methanol solution of 1,3-dihydroxybenzene was not conducted.

Evaluation of Surface Lubricity Retention

The samples produced in Examples 5 and 6 and Comparative Examples 4 and 5 were put to evaluation of surface lubricity retention by the following method. As shown in FIG. 1, a double coated tape was adhered to a glass-made petri dish 2, and each sample 5 of the samples produced in Examples 5 and 6 and Comparative Examples 4 and 5 was fixed on the adhesive surface of the double coated tape. The petri dish 2 was filled up with water 1, and the assembly was put on the friction measuring apparatus (Handy Tribomaster TL201, produced by Trinity Lab Inc.). Then, using a weight 4, a load of 300 g was exerted on a SUS-made spherical probe 3, and frictional resistance was measured while sliding the probe 3 over a distance of 20 mm at a velocity of 1,000 mm/min, repeatedly 20 times. In this case, the measurement was conducted twice (n=2) for each sample, and the measurement results were plotted in graphs, respectively.

Figure 9:
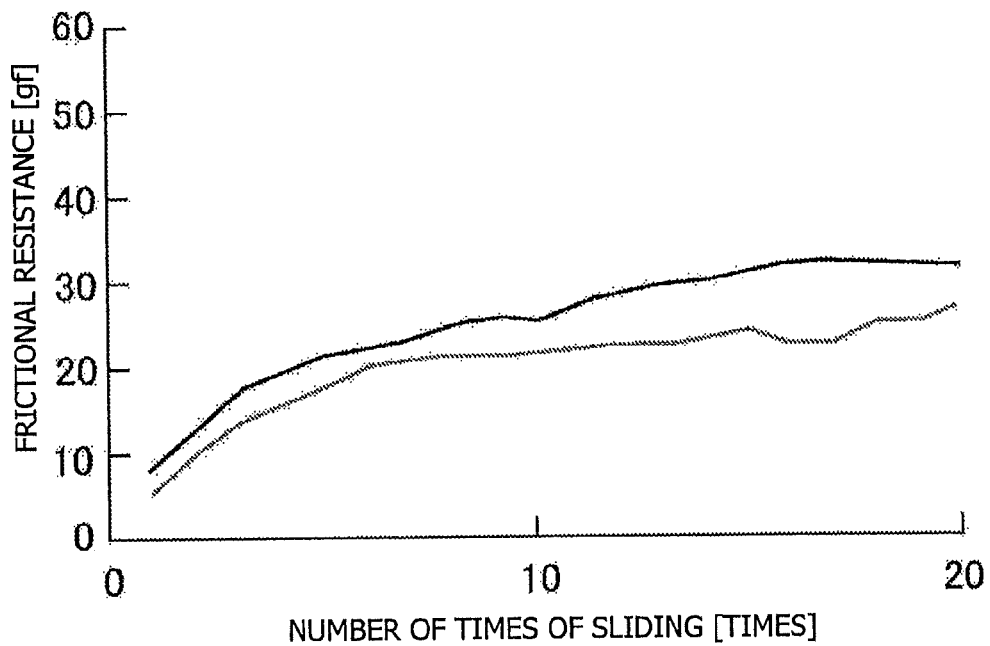
FIG. 9 shows the evaluation result of surface lubricity retention for a sheet (sample) obtained in Example 5.
Figure 10:
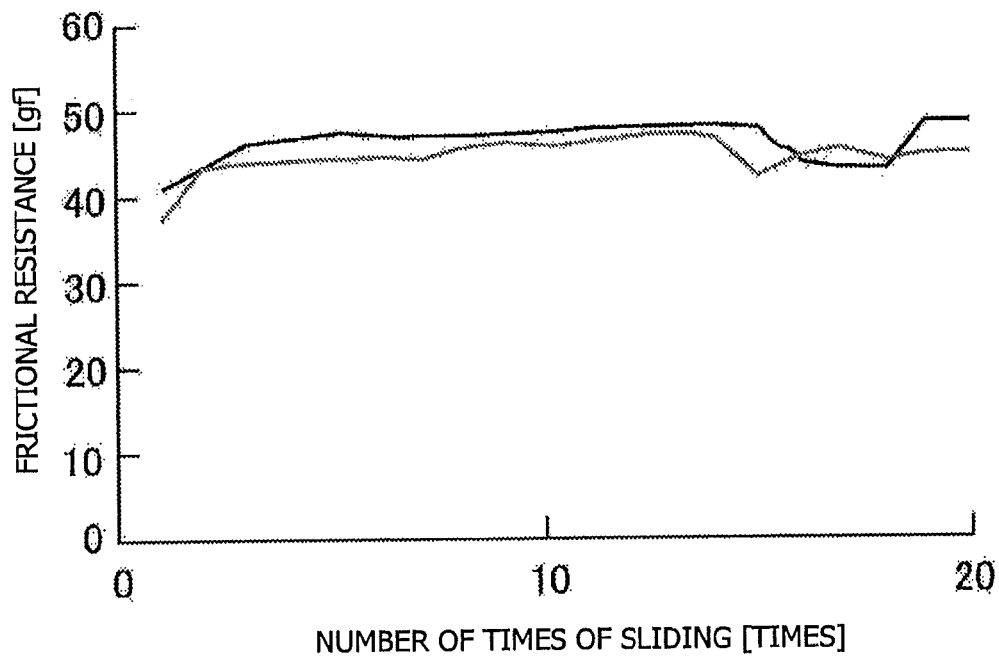
FIG. 10 shows the evaluation result of surface lubricity retention for a sheet (sample) obtained in Comparative Example 4.
Figure 11:
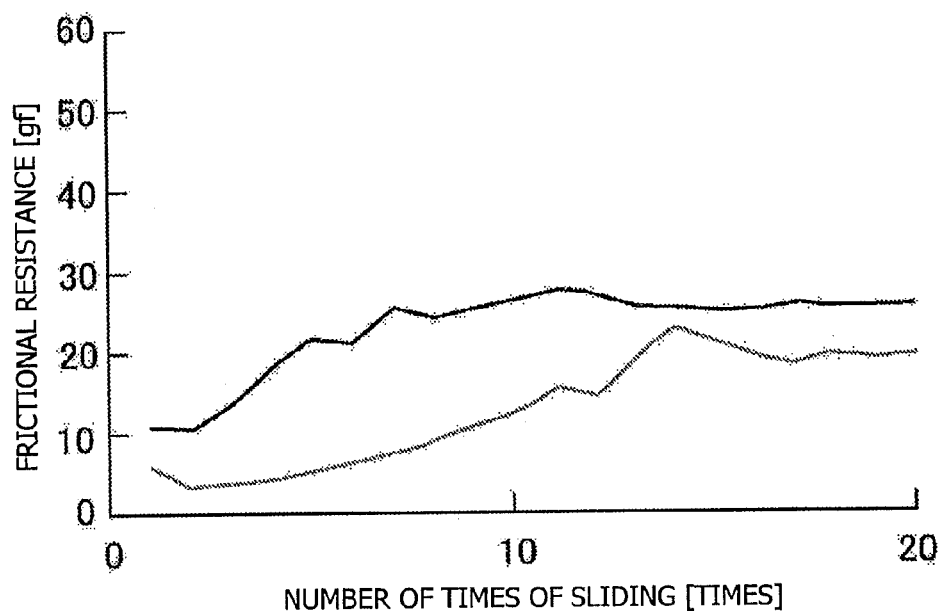
FIG. 11 shows the evaluation result of surface lubricity retention for a sheet (sample) obtained in Example 6.
Figure 12:
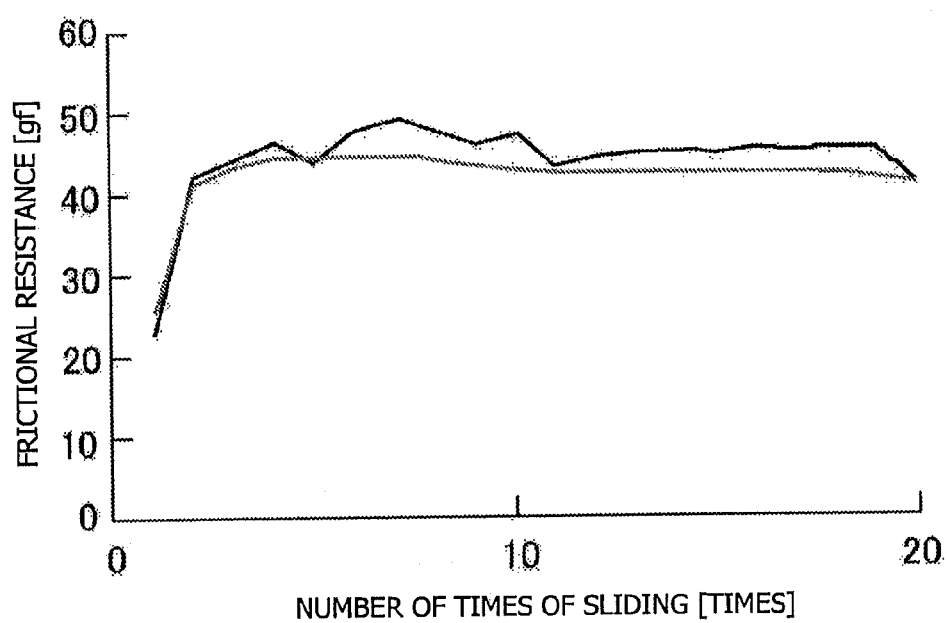
FIG. 12 shows the evaluation result of surface lubricity retention for a sheet (sample) obtained in Comparative Example 5.

The measurement results of surface lubricity retention for the samples produced in Examples 5 and 6 are shown in FIGS. 9 and 11, whereas the measurement results of surface lubricity retention for the samples produced in Comparative Examples 4 and 5 are shown in FIGS. 10 and 12, respectively. In Examples 5 and 6, the samples showed a low value of frictional resistance in the beginning period. On the other hand, in Comparative Examples 4 and 5, the value of frictional resistance was high from the beginning period. This is considered to be because the hydrophilic polymer which is not fixed on the base material is dissolved in water, unlike in Examples 5 and 6.

The principles, preferred embodiment disclosed by way of example and other disclosed aspects of the medical device producing method have been described in the foregoing specification. However, the invention intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method for producing a medical device comprising:
    applying a solution containing a phenolic compound to a medical device, wherein the phenolic compound is 1,3-dihydroxybenzene or t-butylhydroxyanisole, the medical device being sized and configured to be positioned in a living body, the medical device being made of a base material and possessing a surface, with at least a part of the surface being composed of a polyamide;
    the applying of the solution to the medical device comprising applying the solution containing the phenolic compound to the medical device so that the solution containing the phenolic compound contacts the part of the surface of the base material that is composed of the polyamide; and
    coating the base material with a hydrophilic polymer after applying the solution containing the phenolic compound, with the hydrophilic polymer being coated onto the part of the surface of the base material to which is applied the solution containing the phenolic compound.

2. The method for producing a medical device according to claim 1, wherein a concentration of the phenolic compound in the solution is 10 to 75 wt %.

3. The method for producing a medical device according to claim 2, wherein the hydrophilic polymer has a reactive functional group capable of a cross-linking reaction.

4. The method for producing a medical device according to claim 3, wherein the hydrophilic polymer having the reactive functional group capable of the cross-linking reaction is a block copolymer including a block formed from a hydrophilic monomer and a block formed from a monomer having the reactive functional group.

5. The method for producing a medical device according to claim 2, wherein the hydrophilic polymer is formed only from a hydrophilic monomer.

6. The method for producing a medical device according to claim 1, wherein the concentration of the phenolic compound in the solution is 10 to 75 wt %.

7. The method for producing a medical device according to claim 1, wherein the hydrophilic polymer has a reactive functional group capable of a cross-linking reaction.

8. The method for producing a medical device according to claim 7, wherein the hydrophilic polymer having the reactive functional group capable of the cross-linking reaction is a block copolymer including a block formed from a hydrophilic monomer and a block formed from a monomer having the reactive functional group.

9. The method for producing a medical device according to claim 1, wherein the hydrophilic polymer is formed only from a hydrophilic monomer.

10. A method for producing a medical device comprising:
    applying a solution containing a phenolic compound to a base material of which at least a part of a surface is a polyamide, wherein the phenolic compound is 1,3-dihydroxybenzene or t-butylhydroxyanisole; and
    coating the base material with a hydrophilic polymer after applying the solution containing the phenolic compound.

11. The method for producing a medical device according to claim 10, wherein the concentration of the phenolic compound in the solution is 10 to 75 wt %.

12. The method for producing a medical device according to claim 11, wherein the hydrophilic polymer has a reactive functional group capable of a cross-linking reaction.

13. The method for producing a medical device according to claim 12, wherein the hydrophilic polymer having the reactive functional group capable of the cross-linking reaction is a block copolymer including a block formed from a hydrophilic monomer and a block formed from a monomer having the reactive functional group.

14. The method for producing a medical device according to claim 11, wherein the hydrophilic polymer is formed only from a hydrophilic monomer.

15. The method for producing a medical device according to claim 10, wherein the concentration of the phenolic compound in the solution is 10 to 75 wt %.

16. The method for producing a medical device according to claim 10, wherein the hydrophilic polymer has a reactive functional group capable of a cross-linking reaction.

17. The method for producing a medical device according to claim 16, wherein the hydrophilic polymer having the reactive functional group capable of the cross-linking reaction is a block copolymer including a block formed from a hydrophilic monomer and a block formed from a monomer having the reactive functional group.

18. The method for producing a medical device according to claim 10, wherein the hydrophilic polymer is formed only from a hydrophilic monomer.

* * * * *